US008932533B2

(12) United States Patent
Kruglick

(10) Patent No.: US 8,932,533 B2
(45) Date of Patent: Jan. 13, 2015

(54) CYCLONIC CATALYTIC DUCTS

(75) Inventor: Ezekiel Kruglick, Poway, CA (US)

(73) Assignee: Empire Technology Development LLC, Wilmington, DE (US)

( * ) Notice: Subject to any disclaimer, the term of this patent is extended or adjusted under 35 U.S.C. 154(b) by 125 days.

(21) Appl. No.: 12/999,594

(22) PCT Filed: Oct. 1, 2010

(86) PCT No.: PCT/US2010/051180
§ 371 (c)(1),
(2), (4) Date: Dec. 16, 2010

(87) PCT Pub. No.: WO2012/044325
PCT Pub. Date: Apr. 5, 2012

(65) Prior Publication Data
US 2012/0080107 A1 Apr. 5, 2012

(51) Int. Cl.
*B01J 19/08* (2006.01)
*A61L 9/20* (2006.01)

(52) U.S. Cl.
CPC ...................................... *A61L 9/205* (2013.01)
USPC ............ 422/186.3; 422/3; 422/108; 422/121; 137/561 A; 137/590; 137/861

(58) Field of Classification Search
CPC .............. A61L 2/02; A61L 2/08; A61L 2/088; A61L 2/10; A61L 9/16; A61L 9/205; A61L 2202/14
USPC ....... 422/186.3, 3, 108, 121; 137/561 A, 590, 137/861
See application file for complete search history.

(56) References Cited

U.S. PATENT DOCUMENTS

| | | | |
|---|---|---|---|
| 2,074,818 A | 3/1937 | Watson | |
| 5,914,454 A | 6/1999 | Imbaro et al. | |
| 6,425,931 B1 | 7/2002 | Croggon | |
| 7,117,557 B2 | 10/2006 | Bair et al. | |
| 7,131,165 B2 | 11/2006 | Wright et al. | |
| 2004/0046127 A1 | 3/2004 | Wong | |
| 2004/0213710 A1 | 10/2004 | Wong | |
| 2006/0159598 A1* | 7/2006 | Wu | 422/186.3 |
| 2007/0177372 A1 | 8/2007 | Matsuda et al. | |
| 2009/0041632 A1 | 2/2009 | Day et al. | |
| 2009/0166282 A1* | 7/2009 | Dong | 210/251 |
| 2010/0176067 A1* | 7/2010 | Boyd et al. | 210/748.09 |
| 2011/0002815 A1* | 1/2011 | Obee et al. | 422/122 |
| 2012/0076700 A1* | 3/2012 | Liptak | 422/186.3 |

FOREIGN PATENT DOCUMENTS

| | | |
|---|---|---|
| CN | 1524798 A | 9/2004 |
| EP | 1382572 A1 | 1/2004 |

(Continued)

OTHER PUBLICATIONS

Kuo-Pin Yu, et al., Effectiveness of Photocatalytic Filter for Removing Volatile Organic Compounds in the Heating, Ventilation, and Air Conditioning System, Journal of Air & Waste Management Association, vol. 56, May 2006.

(Continued)

*Primary Examiner* — Xiuyu Tai
(74) *Attorney, Agent, or Firm* — Turk IP Law, LLC

(57) ABSTRACT

Implementations and techniques for cyclonic catalytic ducts are generally disclosed.

14 Claims, 7 Drawing Sheets

(56) References Cited

FOREIGN PATENT DOCUMENTS

| | | | |
|---|---|---|---|
| JP | 01-293876 A | | 11/1989 |
| JP | 09-038487 A | | 2/1997 |
| JP | 09-084866 A | | 3/1997 |
| JP | 10-071191 A | | 3/1998 |
| JP | 11-309202 A | | 11/1999 |
| JP | 2000-079324 A | | 3/2000 |
| JP | 2000-325750 A | | 11/2000 |
| JP | 2001-061949 A | | 3/2001 |
| JP | 2002-058728 | * | 2/2002 |
| JP | 2004-141618 A | | 5/2004 |
| JP | 2004-162511 A | | 6/2004 |
| JP | 2005-288397 A | | 10/2005 |
| JP | 2006-142270 A | | 6/2006 |
| JP | 2012507378 A | | 3/2012 |
| WO | 2009109763 | | 9/2009 |

OTHER PUBLICATIONS

Chin, Paul and David F. Ollis, Design Approaches for a Cycling Adsorbent/Photocatalyst System for Indoor Air Purification: Formaldehyde Example, Journal of Air & Waste Management Association, vol. 58: 494-501, Apr. 2008.

Chin, P., et al., "Formaldehyde Removal from Air Via a Rotating Adsorbent Combined with a Photocatalyst Reactor: Kinetic Modeling," Journal of Catalysis, 2006, vol. 237, No. 1, pp. 29-37.

International Search Report for International Application No. PCT/US2010/051180, ISA/AU, mailed on Nov. 18, 2010.

Shiraishi, F., et al., "A Rapid Treatment of Formaldehyde in a Highly Tight Room Using a Photocatalytic Reactor Combined With a Continuous Adsorption and Desorption Apparatus," Chemical Engineering Science, Feb.-Mar. 2003, vol. 58, Issue 3-6, pp. 929-934.

Abou-Helal, M.O. et al., Preparation of TiO2 thing films by spray pyrolysis to be used as a photocatalyst, Applied Surface Science, Jul. 15, 2002, pp. 53-62, vol. 195, issues 1-4, Elsevier.

* cited by examiner

700 A computer program product.

702 A signal bearing medium.

704 at least one of machine-readable instructions, which, if executed by one or more processors, operatively enable a computing device to:

sense a level of volatile organic compounds associated with an air distribution system;

compare the sensed volatile organic compound level with a reference volatile organic compound level; and/or adjust an ultraviolet light level associated with a cyclonic photocatalytic duct based at least in part on the comparison of the sensed volatile organic compound level and the reference volatile organic compound level.

| 706 a computer-readable medium. | 708 a recordable medium. | 710 a communications medium. |

CYCLONIC CATALYTIC DUCTS

CROSS REFERENCE TO RELATED APPLICATIONS

This Application is the National Stage filing under 35 US.C. §371 of PCT Application Ser. No. PCT/US10/51180 filed on Oct. 1, 2010. The disclosure of the PCT Application is hereby incorporated by reference in its entirety.

BACKGROUND

Unless otherwise indicated herein, the approaches described in this section are not prior art to the claims in this application and are not admitted to be prior art by inclusion in this section.

Studies have examined the possibility of applying photocatalytic air purification within the context of standard home or commercial air systems. Several of these studies have focused on providing the photocatalytic action at or near the typical filter stage with largely motionless air. The physical reason for the use of largely motionless air is that long dwell times may be needed for random air action to bring sufficient particles into sufficient contact with the photocatalyst to neutralize significant amounts of pollutants.

SUMMARY

This disclosure is drawn, inter alia, to methods, apparatus, and systems related to implementing cyclonic catalytic ducts.

Some example apparatus related to cyclonic photocatalytic ducts may include a main body, one or more angled input nozzles, a layer of photocatalytic material, and an ultraviolet light source. The main body may have a tubularly shaped inner surface. The one or more angled input nozzles may be located on the inner surface of the main body. The one or more angled input nozzles may be configured to induce cyclonic air flow in the cyclonic photocatalytic duct. The layer of photocatalytic material may coat at least a portion of the inner surface of the main body. The ultraviolet light source may be located within the main body and may be adapted to illuminate at least a portion of the layer of photocatalytic material.

Some example systems related to cyclonic photocatalytic ducts may include a supply fan and a cyclonic photocatalytic duct. The cyclonic photocatalytic duct may be coupled in fluid communication with the supply fan and located downstream from the supply fan. The cyclonic photocatalytic duct may include a main body, one or more angled input nozzles, a layer of photocatalytic material, and an ultraviolet light source. The main body may have a tubularly shaped inner surface. The one or more angled input nozzles may be located on the inner surface of the main body. The one or more angled input nozzles may be configured to induce cyclonic air flow in the cyclonic photocatalytic duct. The layer of photocatalytic material may coat at least a portion of the inner surface of the main body. The ultraviolet light source may be located within the main body and may be adapted to illuminate at least a portion of the layer of photocatalytic material.

Some example methods related to control of cyclonic photocatalytic ducts may include sensing a level of volatile organic compounds associated with an air distribution system. The sensed volatile organic compound level may be compared with a reference volatile organic compound level. The ultraviolet light level associated with a cyclonic photocatalytic duct may be adjusted based at least in part on the comparison of the sensed volatile organic compound level and the reference volatile organic compound level.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

Subject matter is particularly pointed out and distinctly claimed in the concluding portion of the specification. The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

FIG. 7 is an illustration of an example computer program product; and

DETAILED DESCRIPTION

Figure 1:
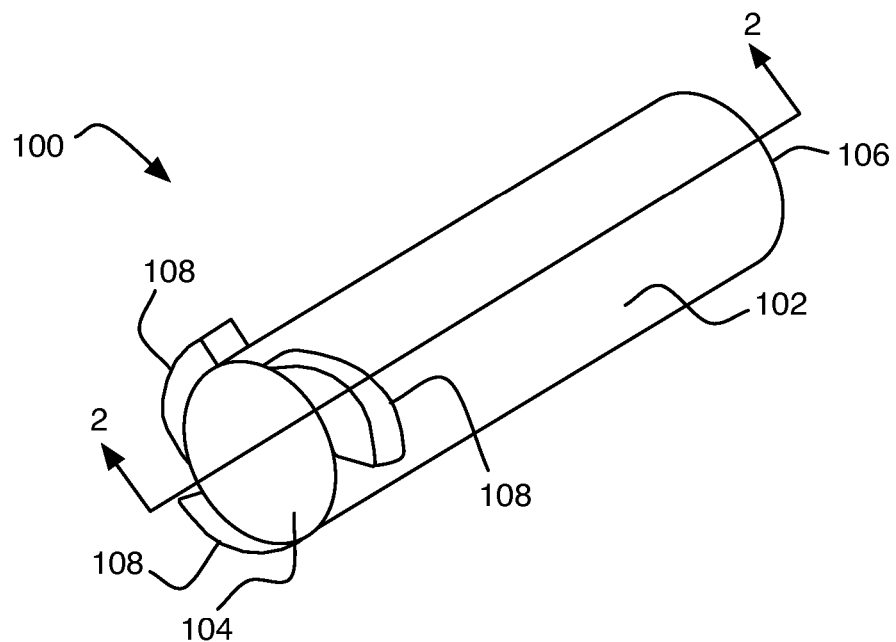
FIG. 1 is an illustration of an example perspective view of a cyclonic photocatalytic duct.

The following description sets forth various examples along with specific details to provide a thorough understanding of claimed subject matter. It will be understood by those skilled in the art, however, that claimed subject matter may be practiced without some or more of the specific details disclosed herein. Further, in some circumstances, well-known methods, procedures, systems, components and/or circuits have not been described in detail in order to avoid unnecessarily obscuring claimed subject matter.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated and make part of this disclosure.

This disclosure is drawn, inter alia, to methods, apparatus, and systems related to implementing cyclonic catalytic ducts.

As noted above, several studies have focused on performing photocatalytic action at or near the typical filter stage with largely motionless air. As will be discussed in greater detail below, cyclonic air flow may be utilized as a way to increase the path length of air traveling through an air distribution system without reducing and/or interrupting air flow. Additionally, cyclonic air flow may also be utilized to encourage pollutants to preferentially make contact with a photocatalytic material lining a duct.

For example, a cyclonic catalytic duct may be oriented and arranged to induce and/or maintain cyclonic airflow as well as be lined with photocatalytic material. As discussed above, such cyclonic airflow may increase the path length of air traveling through the cyclonic catalytic duct. For example, instead of traveling a straight path through ducting, cyclonic airflow may cause the air to take a cyclonic path through the cyclonic catalytic duct by rotating repeatedly around the inner surface of the cyclonic catalytic duct.

Additionally, such a cyclonic catalytic duct may be lined with photocatalytic material. A fixed photocatalytic material may operate as a surface phenomena; accordingly, waiting for diffusion to bounce enough particles against the photocatalytic material may require long time periods or long contact paths. As discussed above, cyclonic airflow may encourage pollutants to preferentially make contact with a photocatalytic material lining the inner surface of the cyclonic catalytic duct. For example, instead of traveling a straight path where pollutants located near the center of the ducting may have a low probability of contacting the inner surface of the ducting, cyclonic airflow may cause the air to take a cyclonic path through the cyclonic catalytic duct encouraging pollutants to preferentially make contact with a photocatalytic material lining the inner surface of the cyclonic catalytic duct.

Further, such a cyclonic catalytic duct may include an ultraviolet light source adapted to illuminate the cyclonic catalytic ducts with ultraviolet light. Such ultraviolet light may be utilized to illuminate the photocatalytic material lining the inner surface of the cyclonic catalytic duct to improve air quality. For example, photocatalytic materials and ultraviolet light may be utilized to accelerate the break down of volatile organic compounds (VOC) (e.g., formaldehyde and other organic contaminants) contained in the air passing through the cyclonic catalytic duct. For example, such VOCs may include, but are not limited to, compounds from one or more categories of approximately five hundred and fifty categories of VOCs recognized by the California Air Resources Board (GARB). Additionally, the combination of photocatalytic materials and ultraviolet light may kill airborne pathogens, such as but not limited to, bacteria and viruses, as well as breaking down other types of airborne pollutants (such as but not limited to carbon monoxide, sulfates, nitrates, and the like).

FIG. 1 is an illustration of an example perspective view of a cyclonic photocatalytic duct that is arranged in accordance with at least some embodiments of the present disclosure. In the illustrated example, a cyclonic photocatalytic duct 100 may include a tubularly shaped main body 102. Main body 102 may have a closed end 104 and an open end 106. Open end 106 may be positioned opposite the closed end 104. Sizing for air ducts may range from about four inches in diameter (e.g., as might be utilized in small homes), to three or four feet in diameter (e.g., as might be utilized in commercial spaces), to tens of feet in diameter (e.g., as might be utilized in really large places like stadiums). Cyclonic photocatalytic duct 100 may be utilized at all such sizes. Main body 102 may be formed from any number of materials including but not limited to metal, plastics, the like, or combinations thereof.

One or more manifolds 108 may extend from main body 102 adjacent to closed end 104. Manifolds 108 may be adapted to receive inlet air into cyclonic photocatalytic duct 100. In one example, manifolds 108 may be positioned one hundred and twenty degrees apart from one another along the circumference of main body 102. Alternatively, more or less manifolds 108 may be positioned equidistantly (or non-equidistantly) along the circumference of main body 102.

Figure 2:
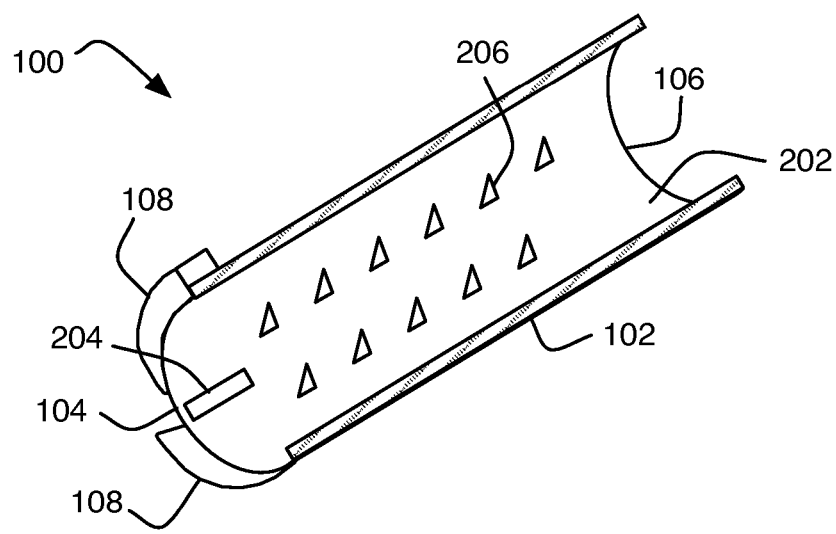
FIG. 2 is an illustration of an example cross-sectional perspective view of a cyclonic photocatalytic duct taken along line 2-2 of FIG. 1.

FIG. 2 is an illustration of an example cross-sectional perspective view of cyclonic photocatalytic duct 100 taken along line 2-2 of FIG. 1 that is arranged in accordance with at least some embodiments of the present disclosure. In the illustrated example, main body 102 may include a tubularly shaped inner surface 202 (e.g., including cylindrical, elliptical, octagonal, or the like). Main body 102 may include an exterior surface of any shape, tubular or otherwise. A layer of photocatalytic material (not illustrated) may coat at least a portion of inner surface 202 of main body 102. In examples utilizing titanium dioxide as a layer of photocatalytic material, a thickness may be determined by what may be suitable to make an adhesive layer (e.g., in a two micrometer to one hundred micrometer range depending on particle size and adhesive method). As used herein, term "photocatalytic material" may refer to one or more substances capable of accelerating the break down of volatile organic compounds (VOC), accelerating the killing of bacteria and/or viruses, and/or breaking down other types of airborne pollutants. Such photocatalytic material may include but is not limited to, elemental photocatalysts such as but not limited to platinum or carbon; compound photocatalysts such as but not limited to titanium dioxide, zinc oxide, or sodium tantalum oxide; organic photocatalysts such as but not limited to poly(p-phenylene) or 2,4,6-triphenylthiapyrylium; the like, or combinations thereof. As used herein, term "accelerating" or "accelerate" may refer to causing faster and/or greater activity, development, progress, advancement, etc. (e.g., accelerating the rapidity and/or the amount of the break down of compounds and/or the killing of organisms) as compared to ambient or pre-existing conditions. For example, the layer of photocatalytic material may include one or more of the following compounds: titanium dioxide, zinc oxide, sodium tantalum oxide, and the like, or combinations thereof. Photocatalytic material may be coated via vapor chemical processing (e.g., chemical vapor deposition), spray pyrolysis, or the like onto inner surface 202 of main body 102. For example, titanium dioxide-type photocatalytic material may be applied by spray pyrolysis as illustrated in "Preparation of TiO2 thin films by spray pyrolysis to be used as a photocatalyst" M O Abou-Helal, W T Seeber—Applied Surface Science, 2002—Elsevier. Alternatively, photocatalytic material may be coated by applying an adhesive (e.g., spray adhesive such as but not limited to 3M brand General Adhesive 45 or the like) onto inner surface 202 of main body 102 and coating the adhesive with granulated or powdered photocatalytic material.

One or more angled input nozzles 204 may be located on inner surface 202 of main body 102. While only a single angled input nozzle 204 is illustrated, it will be appreciated from FIG. 1 and FIG. 2 that in the illustrated example three angled input nozzles 204 may be positioned along the circumference of main body 102. Angled input nozzles 204 may be configured to induce cyclonic air flow in cyclonic photocatalytic duct 100. Individual angled input nozzles 204 may be in fluid communication with individual manifolds 108 adjacent to closed end 104. As used herein, the term "fluid communication" may include gaseous fluid communication (e.g. air or the like). Angled input nozzles 204 may be adapted to receive inlet air via manifolds 108 and direct such air into cyclonic photocatalytic duct 100. In one example, three angled input nozzles 204 may be positioned equidistantly along the circumference of main body 102 (e.g. one hundred and twenty degrees apart from one another along the circumference of main body 102). Alternatively, additional or fewer angled input nozzles 204 may be positioned equidistantly (or non-equidistantly) along the circumference of main body 102.

In the illustrated example, angled input nozzles 204 may individually have an elongated aperture oriented to direct airflow generally tangential to a portion of inner surface 202 of main body 102 that is located directly adjacent such an elongated aperture. In some examples, the size of such an elongated aperture may be governed by the desired airflow and velocity. For example, household units may have elongated aperture on the order of one to thirty centimeters across while much larger or smaller elongated apertures may be utilized depending on the particular implementation (e.g., for industrial applications, etc.). Angled input nozzles 204 may be angled to induce direct airflow generally tangential to inner surface 202 in order to induce cyclonic air flow in cyclonic photocatalytic duct 100. Such angling of angled input nozzles 204 may be done with a very flat angle coming in from an aperture (as is illustrated here) at inner surface 202. Additionally or alternatively, such angling of angled input nozzles 204 may be done with a protruding nozzle (as is illustrated in one example shown in FIG. 5) that enters into the airflow far enough to reach a tangent point (a point where the airflow moves generally perpendicular to a radial line from the center). In other examples, angled input nozzles 204 may include other shapes and/or sizes (e.g., circular, elliptical, or the like) that are configured to direct airflow generally tangential to a portion of inner surface 202 of main body 102 that is located directly adjacent such angled input nozzles 204 to induce cyclonic air flow in cyclonic photocatalytic duct 100.

An ultraviolet light source 206 may be located within main body 102. Ultraviolet light source 206 may be adapted to illuminate at least a portion of the layer of photocatalytic material located on inner surface 202 of main body 102. As used herein the term "ultraviolet light source" may refer to a light source capable of delivering ultraviolet light. For example, ultraviolet light source 206 may include one or more of the following types of light sources: a light emitting diode-type ultraviolet light source, a fluorescent tube-type ultraviolet light source, an incandescent bulb-type ultraviolet light source, a vapor lamp-type ultraviolet light source, and the like, or combinations thereof. In the illustrated example, ultraviolet light source 206 may include a light emitting diode-type ultraviolet light source attached to inner surface 202 of main body 102. Additionally or alternatively, ultraviolet light source 206 may be located externally to main body 102. In such a case, main body 102 may be transparent, translucent, include windows selected to pass ultraviolet light, the like, or combinations thereof.

In operation, cyclonic catalytic ducting 100 may be utilized for indoor air purification and sterilization. Such cyclonic catalytic ducting 100 may be adapted for integration with existing air distribution infrastructure, possibly without adding additional space for machine rooms or new filter areas in buildings. Additionally, cyclonic catalytic ducting 100 may be adapted for integration with existing air distribution infrastructure so as to maintain (or minimally impact) the flow rate of the existing systems.

Figure 3:
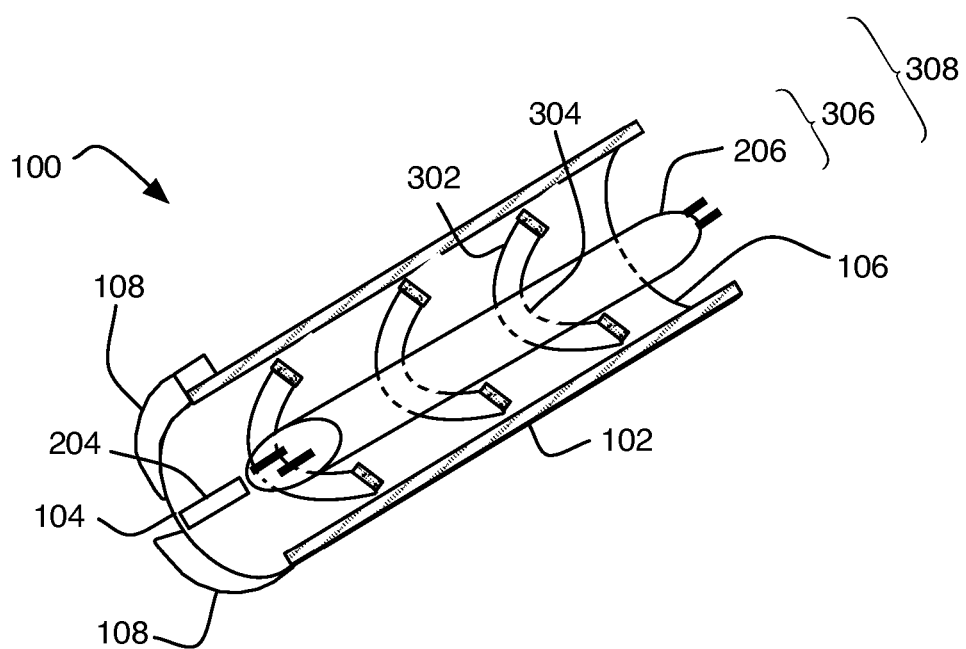
FIG. 3 is an illustration of another example cross-sectional perspective view of a cyclonic photocatalytic duct taken along line 2-2 of FIG. 1.

FIG. 3 is an illustration of another example cross-sectional perspective view of cyclonic photocatalytic duct 100 taken along line 2-2 of FIG. 1 arranged in accordance with at least some embodiments of the present disclosure. In the illustrated example, ultraviolet light source 206 may be suspended by some form of support structure (e.g., a vane, a strut, and/or the like) within main body 102. For example, ultraviolet light source 206 may include a fluorescent tube-type ultraviolet light source suspended within main body 102. As discussed above, ultraviolet light source 206 may include one or more of the following types of light sources: a light emitting diode-type ultraviolet light source, a fluorescent tube-type ultraviolet light source, an incandescent bulb-type ultraviolet light source, a vapor lamp-type ultraviolet light source, and the like, or combinations thereof.

In the illustrated example, ultraviolet light source 206 may be suspended by one or more angled vanes 302 extending from inner surface 202 of main body 102. Additionally or alternatively, angled vanes 302 may be configured to assist cyclonic air flow in cyclonic photocatalytic duct 100. For example angled vanes 302 may be oriented so that the angle of angled vanes 302 is generally in line with the angle of the cyclonic airflow relative to the inner surface 102. For example, angled vanes 302 may be configured to assist cyclonic air flow by steadying the flow before it turns turbulent. Angled vanes 302 may be formed from any number of materials including but not limited to metal, plastics, the like, or combinations thereof.

For example, angled vanes 302 may include an inner edge 304 that is positioned apart from inner surface 102 while not closing off a center portion 306 of the aperture 308 in open end 106. In the illustrated example, fluorescent tube-type ultraviolet light source 206 may be suspended by being supported and/or connected to inner edge 304 at some or all circumferential points. In such an arrangement, ultraviolet light source 206 may oriented to illuminate at least a portion of the layer of photocatalytic material located on inner surface 202 of main body 102. Additionally or alternatively, the layer of photocatalytic material (not illustrated) may coat at least a portion of angled vanes 302.

Additional or alternative angled input nozzles and/or angled vanes may be utilized to maintaining cyclonic flow over distances, around turns, and in ducting branches (e.g., a coaxial-type tube, Y-type, and T-type ducting branches). In such examples, a coupling with additional or alternative angled input nozzles and/or angled vanes (e.g., a coupling similar in structure to cyclonic photocatalytic duct 100) may be used to re-establish the cyclonic flow, and/or the shape (e.g., a coaxial-type tube, Y-type, and T-type ducting branches) of a ducting branch shape may be modified to be more suitable for minimizing the impact on established cyclonic flow. For example, such a coaxial-type tube ducting branch might be utilized to receive flow from a single tube and split the flow coaxially (e.g., with separation between a first central air flow and a second peripheral air flow). Such a coaxial-type tube may have a central air flow (e.g. non-cyclonic air flow) removed at a sharp angle, such as through a pipe (not shown) shaped similarly to a vane 302 elongated along the cyclonic flow.

Figure 4:
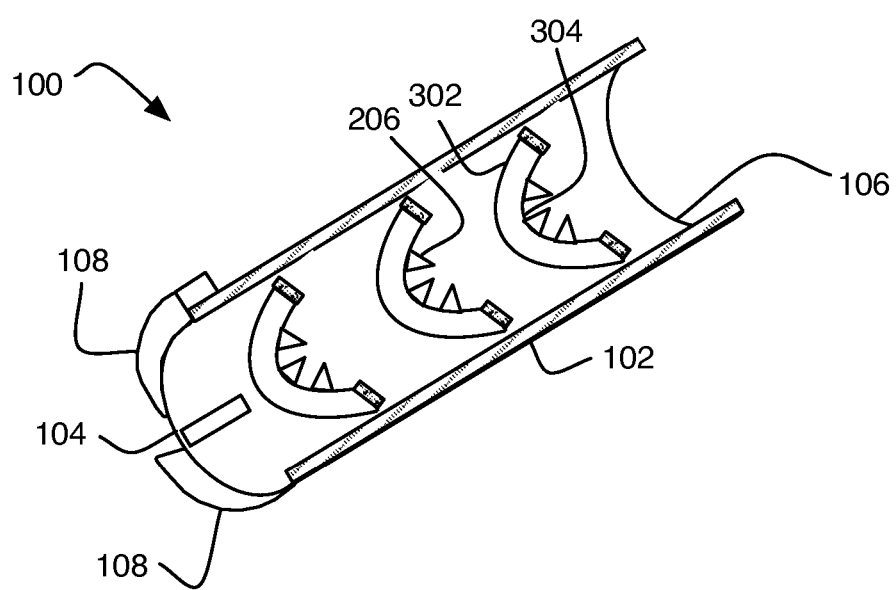
FIG. 4 is an illustration of a further example cross-sectional perspective view of a cyclonic photocatalytic duct taken along line 2-2 of FIG. 1.

FIG. 4 is an illustration of a further example cross-sectional perspective view of cyclonic photocatalytic duct 100 taken along line 2-2 of FIG. 1 arranged in accordance with at least some embodiments of the present disclosure. In the illustrated example, angled vanes 302 may suspend light emitting diode-type ultraviolet light source within main body 102. For example, light emitting diode-type ultraviolet light source 206 may be suspended by being supported and/or connected to inner edge 304 of angled vanes 302. In such an arrangement, ultraviolet light source 206 may be oriented to illuminate at least a portion of the layer of photocatalytic material located on inner surface 202 of main body 102. Additionally or alternatively, the layer of photocatalytic material (not illustrated) may coat at least a portion of angled vanes 302.

Figure 5:
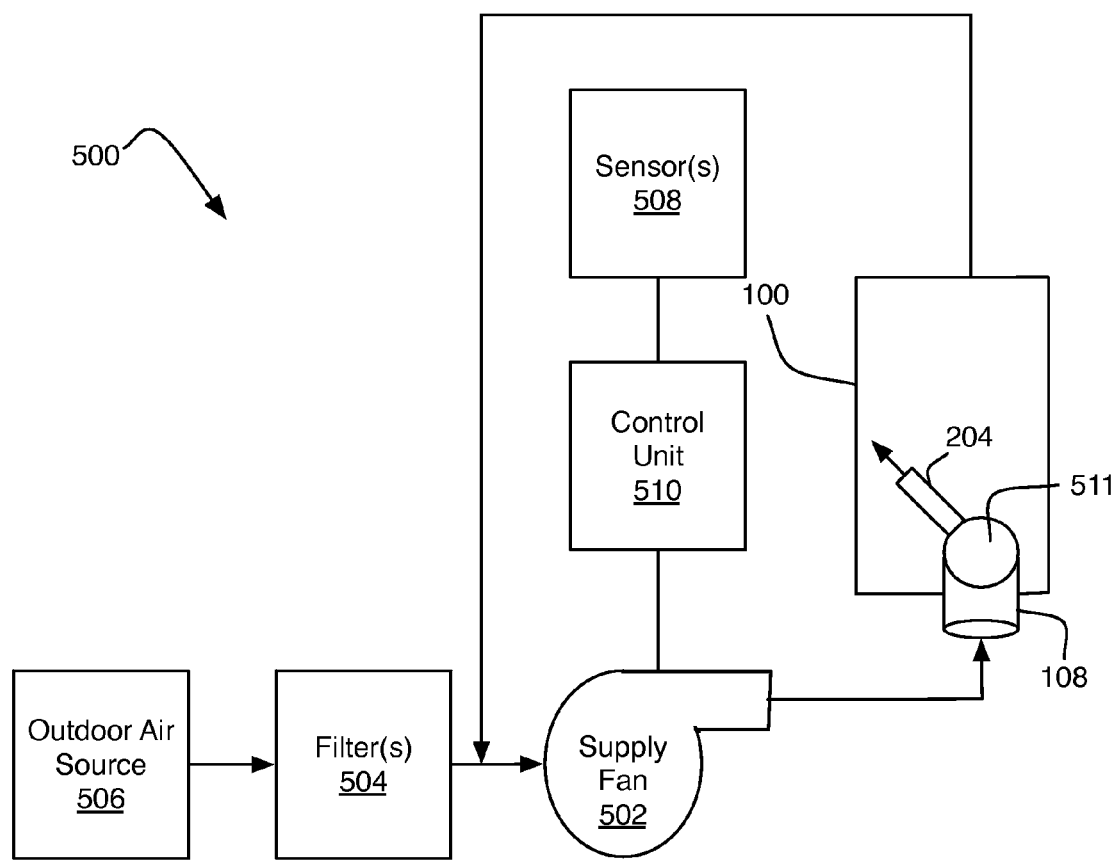
FIG. 5 is an illustration of an example air distribution system including a cyclonic photocatalytic duct.

FIG. 5 is an illustration of an example air distribution system 500 including a cyclonic photocatalytic duct that is arranged in accordance with at least some embodiments of the present disclosure. In the illustrated example, air distribution system 500 may include a supply fan 502 coupled in fluid communication with one or more cyclonic photocatalytic ducts 100. Cyclonic photocatalytic ducts 100 may be located upstream or downstream from supply fan 502.

Examples of air distribution system 500 may include heating ventilating and air conditioning (HVAC) systems, heating systems, ventilation systems, air conditioning systems, and the like, and/or combinations thereof. Such air distribution systems 500 may be utilized in commercial buildings, hospitals, food handling facilities, biological handling facilities, residential buildings, vehicles (e.g., cars and buses), and the like.

Cyclonic photocatalytic ducts 100 may be incorporated into a portion of air distribution system 500 to reduce impact on the overall system (including additional fans or noise). For example, most air in the overall air distribution system 500 may pass through air distribution system 500 multiple times, thus being likely to be exposed to cyclonic photocatalytic ducts 100 at some point.

In one example, one or more filters 504 may be coupled in fluid communication with supply fan 502. Such filters 504 may be located between supply fan 502 and an outdoor air source 506. For example, filters 504 may include one or more of the following filters: high efficiency particulate air filters (HEPA), active carbon filters, high efficiency gas absorption filters (HEGA), ultra low particulate air filters (ULPA), the like, and/or combinations thereof.

In the illustrated example, air distribution system 500 may include one or more sensors 508 that may be configured to sense a level of air impurity associated with air distribution system 500. For example, one or more sensors 508 (such as but not limited to air particle counters, carbon monoxide detectors, VOC sensors, the like, or combinations thereof), alone or in combination with one another, may be configured to sense one or more forms of air impurities, including but not limited to volatile organic compounds, air particles, and/or other types of airborne pollutants.

In the illustrated example, air distribution system 500 may include a control unit 510 (e.g., computing device 800 illustrated at FIG. 8) that may be associated with the sensors 508, supply fan 502, and/or cyclonic photocatalytic ducts 100. Control unit 510 may be configured to adjust an ultraviolet light level associated with cyclonic photocatalytic ducts 100 and/or adjust an air flow associated with supply fan 502 based at least in part on the level of air impurity sensed by sensors 508.

In the illustrated example, cyclonic photocatalytic duct 100 may include angled input nozzles 204 that may be adjustable to direct the gas in a desired spin direction to initiate cyclonic spinning. For example, control unit 510 may be configured adjust an air flow based at least in part on adjusting the orientation of an angle control joint 511, which may change the angle of angled input nozzles 204 and thereby increase or decrease the rate of cyclonic spinning.

Figure 6:
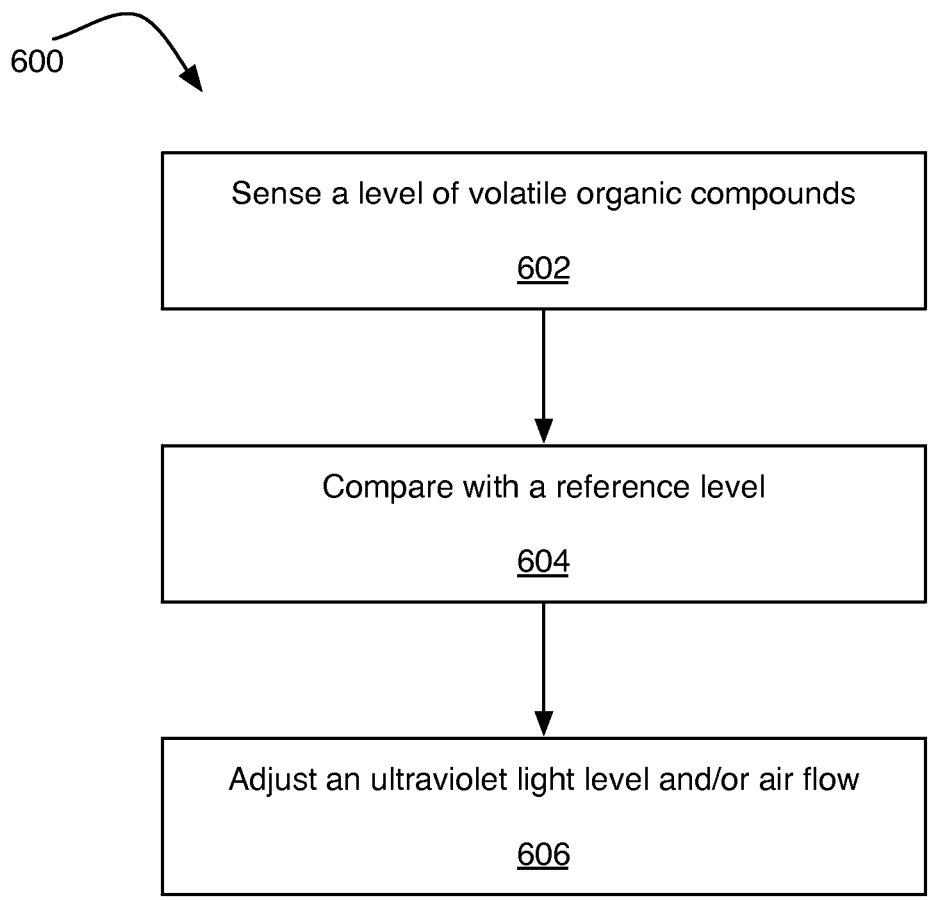
FIG. 6 is an illustration of an example process for operation of an air distribution system.

FIG. 6 is an illustration of an example process for operation of an air distribution system that is arranged in accordance with at least some embodiments of the present disclosure. In the illustrated example, process 600, and other processes described herein, set forth various functional blocks or actions that may be described as processing steps, functional operations, events and/or acts, etc., which may be performed by hardware, software, and/or firmware. Those skilled in the art in light of the present disclosure will recognize that numerous alternatives to the functional blocks shown in FIG. 6 may be practiced in various implementations. For example, although process 600, as shown in FIG. 6, comprises one particular order of blocks or actions, the order in which these blocks or actions are presented does not necessarily limit claimed subject matter to any particular order. Likewise, intervening actions not shown in FIG. 6 and/or additional actions not shown in FIG. 6 may be employed and/or some of the actions shown in FIG. 6 may be eliminated, without departing from the scope of claimed subject matter. Process 600 may include one or more of operations as illustrated by blocks 602, 604, and/or 606.

As illustrated, process 600 may be implemented for management of volatile organic compounds (VOC) during operation of an air distribution system. Processing may begin at operation 602, "sense a level of volatile organic compounds", where a level of volatile organic compounds may be sensed. For example, the level of volatile organic compounds associated with an air distribution system may be sensed via one or more sensors. Such sensors may monitor air circulating within air distribution system, air distributed by air distribution system, or a combination of both.

Processing may continue from operation 602 to operation 604, "compare with a reference level", where the sensed level of volatile organic compounds may be compared to a reference level of volatile organic compounds. As used herein, the term "reference level" may refer to a single value, a single value associated with a tolerance range (e.g., a tolerance range based at least in part on particle counts and/or on parts per million concentration) above and below the single value, or a more complex mathematical relationship representing a desired level of volatile organic compounds.

Processing may continue from operation 604 to operation 606, "adjust an ultraviolet light level and/or air flow", where an ultraviolet light level and/or air flow may be adjusted based at least in part on the comparison of the sensed level of volatile organic compounds to the reference level of volatile organic compounds. For example, in instances where the sensed level of volatile organic compounds is determined to be undesirably and/or unhealthfully high with respect to a target level, the ultraviolet light level may be increased, the air flow may be decreased, or both may occur. Likewise, in instances where the sensed level of volatile organic compounds is determined to be below a target level, the ultraviolet light level may be decreased, the air flow may be increased, or both may occur.

Additionally or alternatively, process 600 may determine an exposure level that units of air circulating through the air distribution system have had to the cyclonic photocatalytic duct. At operation 606, where an ultraviolet light level and/or air flow may be adjusted, such adjustment may be additionally or alternatively based at least in part on such a determined exposure level. For example, such a determined exposure level may be based at least in part on an estimation of the number of times a unit of air has passed through the cyclonic photocatalytic duct during a period of time or the like. At operation 606, where an ultraviolet light level and/or air flow may be adjusted, such adjustment may be additionally or alternatively based at least in part on usage patterns (e.g., actual usage or predicted usage) of occupants. For example, such usage patterns of occupants may indicate that at night in an office a lower ultraviolet light level and/or air flow may be acceptable to take all night to present clean air to people in the morning, whereas during the day, such usage patterns of occupants may indicate that a higher ultraviolet light level and/or air flow may be acceptable to maintain clean air during peak usage.

FIG. 7 illustrates an example computer program product 700 that is arranged in accordance with at least some embodiments of the present disclosure. Computer program product 700 may include a signal bearing medium 702. Signal bearing medium 702 may include one or more machine-readable instructions 704, which, when executed by one or more processors, may operatively enable a computing device to provide the functionality described above with respect to FIG. 6. Thus, for example, referring to the system of FIG. 5, air distribution system 500 may undertake one or more of the actions shown in FIG. 6 in response to instructions 704 conveyed by medium 702.

In some implementations, signal bearing medium 702 may encompass a computer-readable medium 706, such as, but not limited to, a hard disk drive, a Compact Disc (CD), a Digital Video Disk (DVD), a digital tape, memory, etc. In some implementations, signal bearing medium 702 may encompass a recordable medium 708, such as, but not limited to, memory, read/write (R/W) CDs, R/W DVDs, etc. In some implementations, signal bearing medium 702 may encompass a communications medium 710, such as, but not limited to, a digital and/or an analog communication medium (e.g., a fiber optic cable, a waveguide, a wired communication link, a wireless communication link, etc.).

Figure 8:
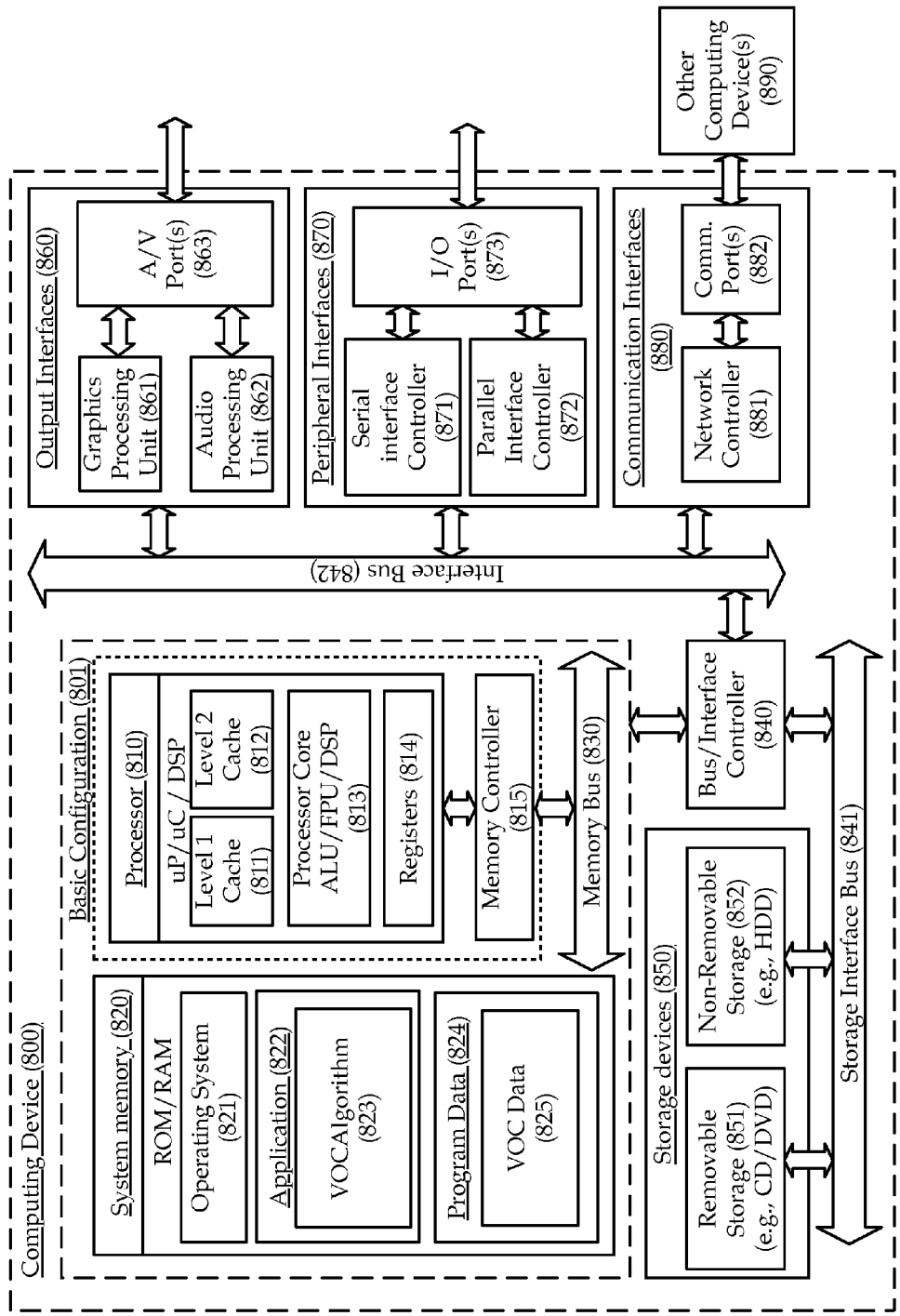
FIG. 8 is a block diagram illustrating an example computing device, all arranged in accordance with at least some embodiments of the present disclosure.
Figure 8:
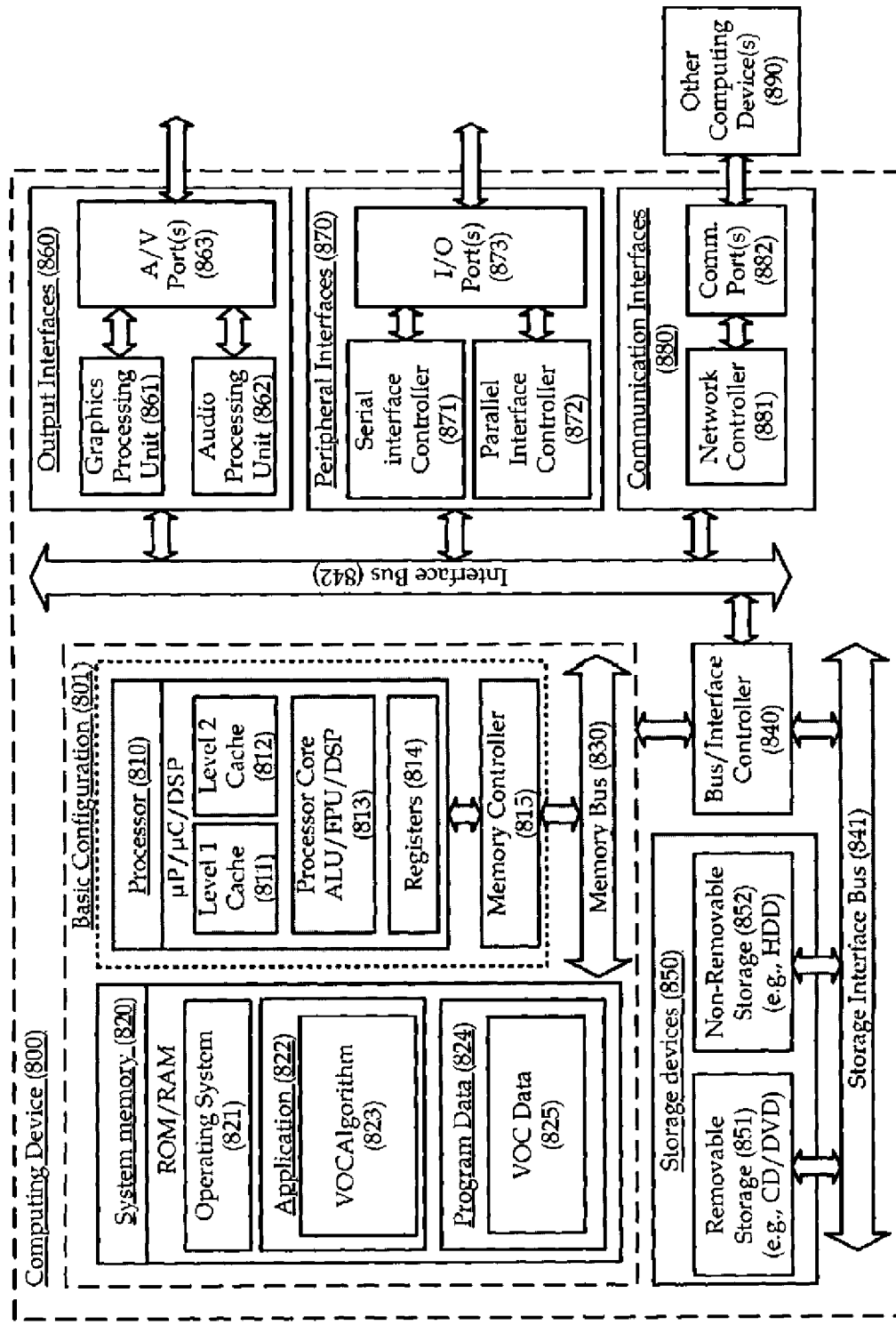

FIG. 8 is a block diagram illustrating an example computing device 800 that is arranged in accordance with at least some embodiments of the present disclosure. In one example basic configuration 801, computing device 800 may include one or more processors 810 and system memory 820. A memory bus 830 can be used for communicating between the processor 810 and the system memory 820.

Depending on the desired configuration, processor 810 may be of any type including but not limited to a microprocessor (µP), a microcontroller (µC), a digital signal processor (DSP), or any combination thereof. Processor 810 can include one or more levels of caching, such as a level one cache 811 and a level two cache 812, a processor core 813, and registers 814. The processor core 813 can include an arithmetic logic unit (ALU), a floating point unit (FPU), a digital signal processing core (DSP Core), or any combination thereof. A memory controller 815 can also be used with the processor 810, or in some implementations the memory controller 815 can be an internal part of the processor 810.

Depending on the desired configuration, the system memory 820 may be of any type including but not limited to volatile memory (such as RAM), non-volatile memory (such as ROM, flash memory, etc.) or any combination thereof. System memory 820 may include an operating system 821, one or more applications 822, and program data 824. Application 822 may include volatile organic compound (VOC) algorithm 823 that can be arranged to perform the functions, actions, and/or operations as described herein including the functional blocks, actions, and/or operations described with respect to process 600 of FIG. 6. Program Data 824 may include VOC data 825 for use with the VOC algorithm 823. In some example embodiments, application 822 may be arranged to operate with program data 824 on an operating system 821 such that implementations of management of volatile organic compounds during operation of an air distribution system may be provided as described herein. This described basic configuration is illustrated in FIG. 8 by those components within dashed line 801.

Computing device 800 may have additional features or functionality, and additional interfaces to facilitate communications between the basic configuration 801 and any required devices and interfaces. For example, a bus/interface controller 840 may be used to facilitate communications between the basic configuration 801 and one or more data storage devices 850 via a storage interface bus 841. The data storage devices 850 may be removable storage devices 851, non-removable storage devices 852, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media may include volatile and nonvolatile, removable and non-removable media implemented in any method or technology for storage of information, such as computer readable instructions, data structures, program modules, or other data.

System memory 820, removable storage 851 and non-removable storage 852 are all examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by computing device 800. Any such computer storage media may be part of device 800.

Computing device 800 may also include an interface bus 842 for facilitating communication from various interface devices (e.g., output interfaces, peripheral interfaces, and communication interfaces) to the basic configuration 801 via the bus/interface controller 840. Example output interfaces 860 may include a graphics processing unit 861 and an audio processing unit 862, which may be configured to communicate to various external devices such as a display or speakers via one or more A/V ports 863. Example peripheral interfaces 870 may include a serial interface controller 871 or a parallel interface controller 872, which may be configured to communicate with external devices such as input devices (e.g., keyboard, mouse, pen, voice input device, touch input device, etc.) or other peripheral devices (e.g., printer, scanner, etc.) via one or more I/O ports 873. An example communication interface 880 includes a network controller 881, which may be arranged to facilitate communications with one or more other computing devices 890 over a network communication via one or more communication ports 882. A communication connection is one example of a communication media. Communication media may typically be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), infrared (IR) and other wireless media. The term computer readable media as used herein may include both storage media and communication media.

Computing device 800 may be implemented as a portion of a small-form factor portable (or mobile) electronic device such as a cell phone, a personal data assistant (PDA), a personal media player device, a wireless web-watch device, a personal headset device, an application specific device, or a hybrid device that includes any of the above functions. Computing device 800 may also be implemented as a personal computer including both laptop computer and non-laptop computer configurations. In addition, computing device 800 may be implemented as part of a wireless base station or other wireless system or device.

Some portions of the foregoing detailed description are presented in terms of algorithms or symbolic representations of operations on data bits or binary digital signals stored within a computing system memory, such as a computer memory. These algorithmic descriptions or representations are examples of techniques used by those of ordinary skill in the data processing arts to convey the substance of their work to others skilled in the art. An algorithm is here, and generally, is considered to be a self-consistent sequence of operations or similar processing leading to a desired result. In this context, operations or processing involve physical manipulation of physical quantities. Typically, although not necessarily, such quantities may take the form of electrical or magnetic signals capable of being stored, transferred, combined, compared or otherwise manipulated. It has proven convenient at times, principally for reasons of common usage, to refer to such signals as bits, data, values, elements, symbols, characters, terms, numbers, numerals or the like. It should be understood, however, that all of these and similar terms are to be associated with appropriate physical quantities and are merely convenient labels. Unless specifically stated otherwise, as apparent from the following discussion, it is appreciated that throughout this specification discussions utilizing terms such as "processing," "computing," "calculating," "determining" or the like refer to actions or processes of a computing device, that manipulates or transforms data represented as physical electronic or magnetic quantities within memories, registers, or other information storage devices, transmission devices, or display devices of the computing device.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In some embodiments, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a flexible disk, a hard disk drive (HDD), a Compact Disc (CD), a Digital Video Disk (DVD), a digital tape, a computer memory, etc.; and a transmission type medium such as a digital and/or an analog communication medium (e.g., a fiber optic cable, a waveguide, a wired communication link, a wireless communication link, etc.).

The herein described subject matter sometimes illustrates different components contained within, or connected with, different other components. It is to be understood that such depicted architectures are merely examples and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

While certain example techniques have been described and shown herein using various methods and systems, it should be understood by those skilled in the art that various other modifications may be made, and equivalents may be substituted, without departing from claimed subject matter. Additionally, many modifications may be made to adapt a particular situation to the teachings of claimed subject matter without departing from the central concept described herein. Therefore, it is intended that claimed subject matter not be limited to the particular examples disclosed, but that such claimed subject matter also may include all implementations falling within the scope of the appended claims, and equivalents thereof.

What is claimed:

1. A cyclonic photocatalytic duct, comprising:
a main body, wherein the main body has a tubularly shaped inner surface;
an angled input nozzle located on the inner surface of the main body, wherein the angled input nozzle is configured to induce cyclonic air flow at an angle tangential to a point on the inner surface that is located directly adjacent to the angled input nozzle and to redistribute particles from air in the cyclonic air flow to the inner surface;
one or more angled vanes extending from the inner surface of the main body and oriented generally in line with the angle of the cyclonic air flow, the one or more angled vanes configured to assist the cyclonic air flow by steadying the cyclonic air flow before the cyclonic air flow becomes turbulent in the cyclonic photocatalytic duct, a control unit configured to adjust an orientation of an angle control joint to alter an angle of the angled input nozzle to one of increase and decrease a rate of the cyclonic air flow based on one or more of a sensed level of volatile organic compounds, a determined exposure level of the air to the cyclonic photocatalytic duct, and a usage pattern of occupants;
a layer of photocatalytic material coating at least a portion of the inner surface of the main body; and
an ultraviolet light source located within the main body, the ultraviolet light source adapted to illuminate at least a portion of the layer of photocatalytic material, wherein the control unit is further configured to adjust an ultraviolet light level associated with the ultraviolet light source based on one or more of the sensed level of volatile organic compounds, the determined exposure level of the air to the cyclonic photocatalytic duct, and the usage pattern of occupants.

2. The cyclonic photocatalytic duct of claim 1, wherein the ultraviolet light source comprises a fluorescent tube-type ultraviolet light source suspended within the main body.

3. The cyclonic photocatalytic duct of claim 1, wherein the ultraviolet light source comprises a light emitting diode-type ultraviolet light source attached to the inner surface of the main body.

4. The cyclonic photocatalytic duct of claim 1 wherein the ultraviolet light source comprises a fluorescent tube-type ultraviolet light source suspended within the main body via the one or more angled vanes.

5. The cyclonic photocatalytic duct of claim 1, wherein the ultraviolet light source comprises a light emitting diode-type ultraviolet light source suspended within the main body via the one or more angled vanes.

6. The cyclonic photocatalytic duct of claim 1, wherein the layer of photocatalytic material comprises one or more of the following compounds: titanium dioxide, zinc oxide, and sodium tantalum oxide.

7. The cyclonic photocatalytic duct of claim 1, wherein the ultraviolet light source comprises one or more of the following types of light sources: a light emitting diode-type ultraviolet light source, a fluorescent tube-type ultraviolet light source, an incandescent bulb-type ultraviolet light source, and a vapor lamp-type ultraviolet light source.

8. The cyclonic photocatalytic duct of claim 1, wherein the main body has a closed end located adjacent to the angled input nozzle and an open end located opposite the closed end.

9. The cyclonic photocatalytic duct of claim 1, wherein the angled input nozzle comprises an elongated aperture oriented to direct airflow at the angle tangential to the point on the inner surface.

10. The cyclonic photocatalytic duct of claim 1, wherein the sensed level of volatile organic compounds is compared with a reference level of volatile organic compounds associated with the air to determine if at least one of the rate of the cyclonic air flow and the light level associated with the ultraviolet light source are adjusted.

11. The cyclonic photocatalytic duct of claim 10, wherein at least one of the light level associated with the ultraviolet light source is increased and the rate of the cyclonic air flow air is decreased in response to a determination that the sensed level of volatile organic compounds is high in comparison to the reference level of volatile organic compounds.

12. The cyclonic photocatalytic duct of claim 10, wherein at least one of the light level associated with the ultraviolet light source is decreased and the rate of the cyclonic air flow air is increased in response to a determination that the sensed level of volatile organic compounds is low in comparison to the reference level of volatile organic compounds.

13. The cyclonic photocatalytic duct of claim 1, wherein the determined exposure level of the air to the cyclonic photocatalytic duct is based on an estimation of a number of times a unit of the air has passed through the cyclonic photocatalytic duct during a period of time.

14. The cyclonic photocatalytic duct of claim 1, wherein the usage pattern of occupants is one of a predicted usage pattern and an actual usage pattern.

* * * * *

UNITED STATES PATENT AND TRADEMARK OFFICE
CERTIFICATE OF CORRECTION

PATENT NO. : 8,932,533 B2
APPLICATION NO. : 12/999594
DATED : January 13, 2015
INVENTOR(S) : Kruglick It is certified that error appears in the above-identified patent and that said Letters Patent is hereby corrected as shown below:

In the Drawings

In the drawing sheet, consisting of Fig. 8, should be deleted to be replaced with the drawing sheet, consisting of Fig. 8, as shown on the attached page.

In the Specification

In Column 3, Line 49, delete "(GARB)." and insert -- (CARB). --, therefor.

In Column 11, Line 59, delete "and or" and insert -- and/or --, therefor.

In the Claims

In Column 14, Line 12, in Claim 4, delete "claim 1" and insert -- claim 1, --, therefor.

Signed and Sealed this
Twenty-first Day of July, 2015

Michelle K. Lee
*Director of the United States Patent and Trademark Office*